United States Patent [19]

Housmans et al.

[11] Patent Number: 5,406,001
[45] Date of Patent: Apr. 11, 1995

[54] METHOD FOR THE CONTINUOUS PREPARATION OF A MIXTURE OF A CYCLOALKANONE, A CYCLOALKANOL AND A CYCLOALKYLHYDROPEROXIDE

[75] Inventors: Johannes G. H. M. Housmans, Maasbracht; Ubaldus F. Kragten, Beek, both of Netherlands

[73] Assignee: DSM N.V., Netherlands

[21] Appl. No.: 166,344

[22] Filed: Dec. 15, 1993

[30] Foreign Application Priority Data

Dec. 16, 1992 [BE] Belgium .................................. 9201101

[51] Int. Cl.$^6$ .............................................. C07C 45/33
[52] U.S. Cl. ..................................... 568/357; 568/570; 568/836; 568/821; 568/700
[58] Field of Search ............... 568/357, 836, 570, 821, 568/700

[56] References Cited

U.S. PATENT DOCUMENTS 3,949,004 4/1976 Sorgenti et al. ................. 568/570
5,220,075 6/1993 Emlen ............................... 568/570

FOREIGN PATENT DOCUMENTS 686329 5/1982 U.S.S.R. ............................. 568/370

Primary Examiner—James H. Reamer
Attorney, Agent, or Firm—Cushman, Darby & Cushman

[57] ABSTRACT

The present invention relates to a method for the continuous preparation of a mixture of a cycloalkanone, a cycloalkanol and a cycloalkylhydroperoxide. In the method, a cycloalkane, corresponding to the cycloalkenone, cycloalkenol and cycloalkylhydroperoxide, is oxidized in a continuous process, with the aid of an oxygen-containing gas, in the absence of a metal catalyst, at a temperature of between 130° C. and 200° C. The oxidation is at least partly carried out in the presence of between 0.002 and 2 mmol of a phenolic compound per kg of reaction mixture (mmol/kg).

16 Claims, 1 Drawing Sheet

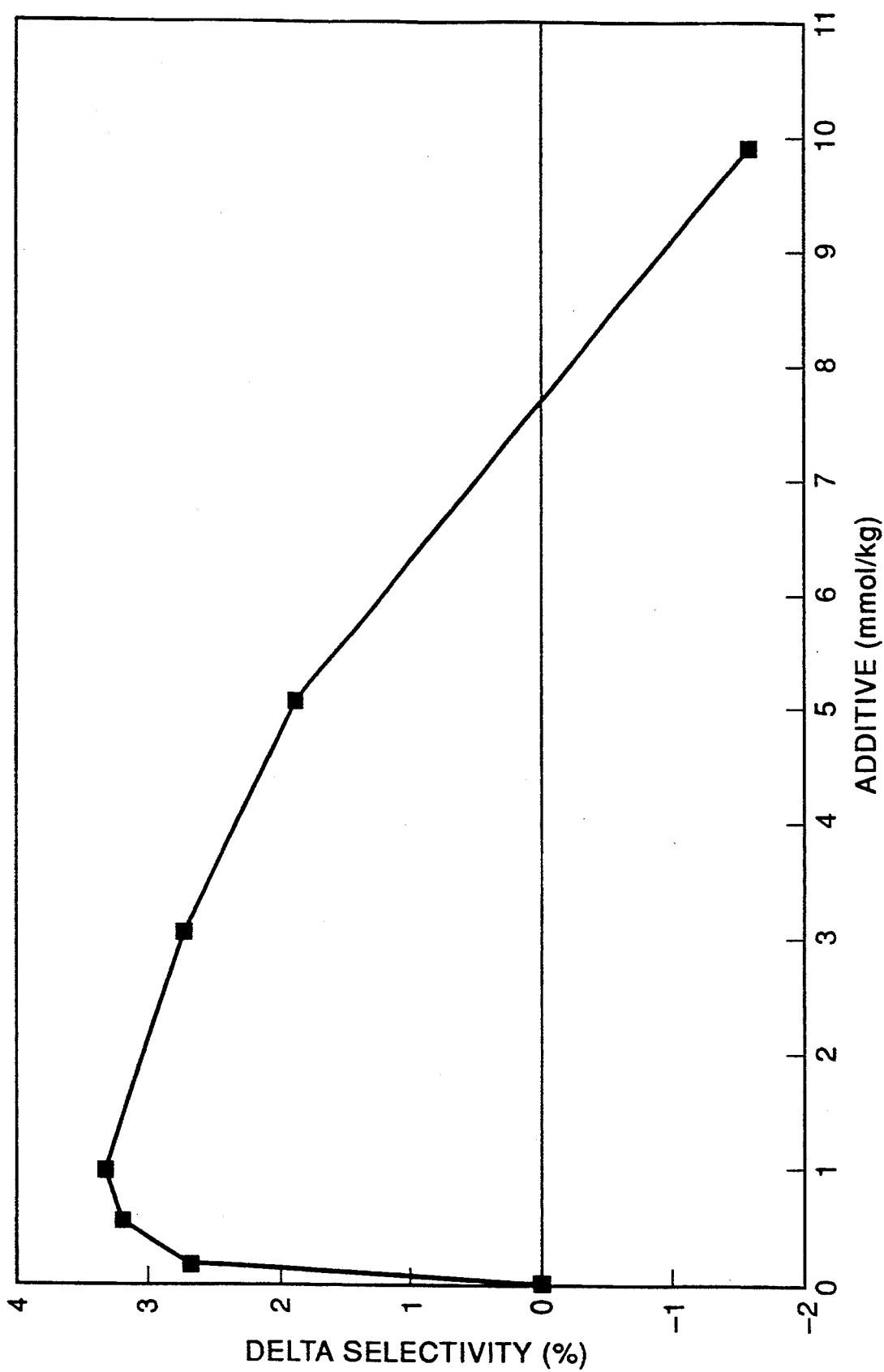

METHOD FOR THE CONTINUOUS PREPARATION OF A MIXTURE OF A CYCLOALKANONE, A CYCLOALKANOL AND A CYCLOALKYLHYDROPEROXIDE

FIELD OF THE INVENTION

The invention relates to a method for the continuous preparation of a mixture of a cycloalkanone, a cycloalkanol and a cycloalkylhydroperoxide. A cycloalkane corresponding to the cyclalkenone, cycloalkenol and cycloalkylhydroperoxide is oxidized, in a continuous process, with the aid of an oxygen-containing gas, in the absence of a metal catalyst, at a temperature of between 130° C. and 200° C.

Background Information

A method for the preparation of a mixture of cyclohexanone, cyclohexanol and cyclohexyl hydroperoxide in a continuous process is described in EP-A-0092867. In that process, cyclohexane is oxidized with a gas containing molecular oxygen to form an oxidation mixture containing cyclohexylhydro peroxide and treating the oxidation mixture at a temperature of 70° C. to 115° C. with a metal salt in the presence of an aqueous solution of an alkali metalhydroperoxide.

A drawback of this known method is that the selectivity of the oxidation reaction towards the desired products (cyclohexanone, cyclohexanol and cyclohexylhydroperoxide) is relatively and undesirably low, and consequently a significant and undesired amount of by-products is formed.

The use of a phenolic compound and the uncatalyzed oxidation of cyclododecane is described in an article in *Petroleum Chemistry (USSR)*, 3(4): 295–301 (1963). This article describes an investigation into the reaction mechanism of the oxidation of cyclododecane. A phenolic compound is added to a batch process after a portion of the cyclododecane has already oxidized. The article contains no indication that the addition of such a phenolic compound in a continuous process could result in an increase in the selectivity.

In SU-A-686329 a method is disclosed for obtaining cyclododecylhydroperoxide by oxidation of cyclododecane in the presence of 0.01–30 wt. % of a phenolic compound at 130°–180° C. As reported, the experiments were apparently conducted with 1 wt. % (1170 mmol/kg) phenol, 2.5 wt. % (230 mmol/kg) cresol and 0.2 wt. % (18 mmol/kg) resorcinol.

In an article in *Kinetics and Catalysis (USSR)*, 1(1): 46–52 (1966), phenol and α-naphthol are mentioned and described as inhibitors in the catalyzed oxidation of n-decane.

The use of phenolic or dihydroxybenzene-like compounds during the metal-catalyzed oxidation of cyclohexane with the objective, increasing the selectivity is described in SU-A-197555. The oxidation reaction disclosed in SU-A-197555 is catalyzed with the aid of a metal catalyst at a temperature of between 200° C. and 250° C. and results in a mixture of cyclohexanol and cyclohexanone. In addition, according to the examples of SU-A-197555, a large amount of phenolic compound is used per kg of reaction mixture (90 to 140 mmol/kg).

Summary And Objects Of The Present Invention

An object of the present invention is to provide a method in which the selectivity of the cycloalkane oxidation reaction towards desired products is higher than towards undesired products.

In particular, an object of the present invention is to provide a method in which the selectivity towards cycloalkylhydroperoxide is higher than achieved with conventional processes.

It is a further object of the present invention to provide a process with a higher selectivity to the desired product without reduction in reaction rates to that product.

The present invention achieves these objectives because the oxidation is at least partly carried out in the presence of an unexpectedly low but surprisingly effective amount of a phenolic compound. The amount of phenolic compound can range between 0.002 and 2 mmol of a phenolic compound per kg of reaction mixture (mmol/kg), and preferably ranges between about 0.01 and about 1 mmol of a phenolic compound per kg of reaction mixture.

It has been found that when the method according to the invention is used, the selectivity of the oxidation reaction towards a cycloalkanone, a cycloalkanol and, in particular, towards a cycloalkylhydroperoxide is surprisingly higher, without the reaction rate being significantly lower than when no phenolic compound is present.

It is also quite unexpected that the oxidation reaction of a cycloalkane, according to the present invention, is hardly slowed by the addition of the phenolic compound.

BRIEF DESCRIPTION OF THE FIGURE

FIG. 1 is a graph showing the concentration of a phenolic compound (2,6 di-tert-butylphenol) in mmol/kg of reaction mixture on the x axis versus the change (delta) absolute persentage of the selectivity of cyclodedanol, cyclododecanone, cyclododecyihydroperoxide on the y axis in comparison to a situation in which no phenolic additive is present.

DETAILED DESCRIPTION OF THE INVENTION

In general, the present unvention relates to the oxidation of cycloalkanes having between 5 and 20 carbon atoms in the absence of metal catalysts but in the presence of small but surprisingly effective amounts of at least one phenolic compound. In particular, the invention relates to the oxidation of cycloalkanes having between 6 and 12 carbon atoms. Examples of suitable cycloalkanes include cyclohexane, cyclooctane and cyclododecane. More specifically, the invention relates to the oxidation of cyclohexane to obtain cyclohexanol, cyclohexanone and cyclohexylhydroperoxide.

The phenolic compound in the present invention contains one or more groups according to Formula (I)

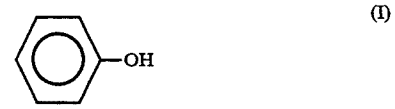

and is soluble in the cycloalkane under reaction conditions.

The phenolic compound is preferably an organic compound having a molecular weight of less than 1000 and having 1–5 aromatic rings.

A suitable group of phenolic compounds according to Formula (I) is represented by Formula (II):

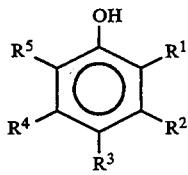

wherein each of $R^1$ through $R^5$ can, independently of one another, represent an —O—$R^6$ group or an $R^7$ group, where $R^6$ and $R^7$ can, independently of one another, represent H or organic groups having between 1 and 30 carbon atoms, whether or not substituted with one or more ether, carbonyl, hydroxyl, amine, amide and ester groups, and/or wherein $R^1$ and $R^2$, or $R^2$ and $R^3$, or $R^3$ and $R^4$, or $R^4$ and $R^5$ can together constitute an aliphatic or aromatic ring having 5, 6, 7, 8, 10 or 12 carbon atoms.

Examples of suitable phenolic compounds, which may or may not be substituted, include, among others, phenol, 2,6-ditertiary-butylphenol, 2,6-ditertiary-butyl-4-methyl-phenol, m-cresol, bisphenol-A, biphenol, p-tertiary-butylphenol, 2-hydroxynaphthalene, 2,6-dimethylphenol, 2,4-ditertiary-butylphenol, 2,4,6-tritertiary-butylphenol, 2,4-dimethyl-6-tertiary-butylphenol, 1-hydroxynaphthalene, hydroquinone, pyrocatechol, resorcinol, p-phenoxyphenol and o-phenylphenol. Preferably, m-cresol, 2,4-ditertiary-butylphenol, 2,6-ditertiary-butylphenol and phenol are used.

Mixtures of the aforementioned phenolic compounds can also be used. Mixtures of phenolic compounds that are prepared during the preparation of a specific phenolic compound can, for example, be used advantageously because further purification is then not required.

The concentration of phenolic compound is generally less than 2 mmol/kg, preferably less than 1 mmol/kg and, in particular is less than 0.9 mmol/kg. The concentration of phenolic compound is generally greater than 0.002 mmol/kg, is preferably greater than 0.01 mmol/kg and, more preferably, is greater than 0.05 mmol/kg. The invention also relates to a process wherein the concentration of phenolic compound is less than 0.01 wt. % relative to the reaction mixture.

The above mentioned concentrations are the concentrations based on the amount of phenolic compound fed to the reaction mixture. The actual average concentration during the oxidation reaction is lower than an above mentioned concentration because at least some portion of the phenolic compound is consumed during the oxidation.

Surprisingly the inventors have discovered that a significantly lower amount of phenolic compound than disclosed in the SU-A-686239 experiments has a remarkably favorably beneficial effect on the selectivity to cycloalkanone, cycloalkanol and cycloalkyhydroperoxide and, more particularly to cyclohexanone, cyclohexanol and cyclohexylhydroperoxide. It is surprising that the addition of small amounts of phenolic compound to an uncatalyzed oxidation of a cycloalkane conducted at a temperature less than about 200° C. has a positive effect with respect to the selectivity at the same degree of conversion.

The temperature at which the oxidation is carried out is generally between 130° C. and 200° C. The temperature is preferably higher than 160° C. and lower than 190° C.

The pressure at which the oxidation is carried out generally lies between 0.1 and 5 MPa. The pressure is preferably higher than 0.4 MPa and lower than 2.5 MPa. In the case where cyclohexane is oxidized, the pressure will generally be higher than 0.6 MPa and lower than 2.0 MPa.

The oxidation is carried out in a continuous mode and preferably takes place in a system of reactors connected in series or in a compartmentalized tube reactor. The reaction is generally carried out autothermally or by controlling the temperature. The temperature is generally controlled by regulating the heat of reaction by discharging a stream of gas, by intermediate cooling or by other methods known to persons skilled in the art.

In order to ensure that transition metals (which promote the decomposition of cycloalkylhydroperoxide) do not become part of the mixture to be oxidized, reactors with an inert inside wall are preferred chosen. To this end, reactors, for example, can be used having an inside wall of passivated steel, aluminum, tantalum, glass or enamel. This is particularly important in the case of small production capacities, in which case the wall surface versus the liquid volume is disadvantageous. In the case of large capacities, separate inertization of the wall is not absolutely necessary. It will be clear that if a negligible amount of metal ions become part of the oxidation mixture, which have no essential influence on the reaction, then, within the framework of the present invention, an uncatalyzed cycloalkane oxidation reaction is occurring. In contrast, with the uncatalyzed cycloalkane oxidation, the catalyzed oxidation—which generally involves the addition of a metal such as cobalt and chromium—yields a reaction mixture with relatively little cycloalkylhydroperoxide relative to cycloalkanone plus cycloalkanol.

Generally, the product of the uncatalyzed oxidation of cyclohexane comprises at least an amount of cyclohexylhydroperoxide in wt. % that is comparable with the amount of cyclohexanol+cyclohexanone in wt. %. Often, the mixture contains more than two times as much cyclohexylhydroperoxide as cyclohexanol plus cyclohexanone after the reaction. In contrast with this, the catalyzed oxidation yields a mixture that contains less than 50% cyclohexylhydroperoxide relative to the amount of cyclohexanol plus cyclohexanone in wt. %. Often, there is even less than 40% peroxide relative to the amount of cyclohexanol plus cyclohexanone in wt. %.

The concentration of cycloalkylhydroperoxide in the reaction mixture, as it leaves the (last) oxidation reactor, is generally between 0.1 and 8.0 wt. %. The cycloalkanone concentration of this mixture is generally between 0.1 and 10 wt. %. The cycloalkanol concentration of this mixture is generally between 0.1 and 15 wt. %. The degree of conversion of cycloalkane relative to this reaction mixture is generally between 0.5 and 25%. The degree of conversion of cyclohexane is generally between 2 and 6%.

In the case of a series of connected reactors or a compartmentalized tube reactor, the phenolic compound can be supplied separately to each reactor (or compartment). It has been found that it is preferable if the concentration of phenolic compound in the first reactor or reactors is relatively lower than the concentration in the last reactor or reactors. It may also be advantageous to supply a phenolic compound to one or more reactors, only, and not to all of the reactors. For instance the phenolic compound can be supplied to a second reactor. The manner and suitable means for introducing the phenolic compound care known to those skilled in the art.

Oxygen as such, air, with increased or reduced oxygen content, or oxygen mixed with nitrogen or another inert gas, can be used as the oxygen-containing gas. Air is preferable, but the air can be mixed with extra inert gas to prevent the risk of explosions. In general, in order to prevent the risk of explosion, oxygen-containing gas is fed to the reactors, in such a manner, that the concentration of oxygen in the offgas remains below the explosion limit. The supplied amount of oxygen (calculated as pure oxygen) is generally between 0.1 and 50 Nl per 1 of cycloalkane. This amount is dependent on the reaction rate, and oxygen is preferably present in a small excess but this is not critical because the amount of oxygen is generally not limiting.

The oxidation products are useful, separately or as a mixture, in many applications. Cyclohexylhydroperoxide can, for example, be used as an oxidizer in the preparation of alkane epoxide from a corresponding alkene. The cyclohexylhydroperoxide in the mixture can also be decomposed to obtain a mixture of cyclohexanone and cyclohexanol. This so-called K/A mixture is a product that is used, for example, in the preparation of adipic acid. The decomposition of the cyclohexylhydroperoxide generally takes place after cooling of the mixture, under the influence of a transition-metal catalyst such as cobalt or chromium. Preferably, the decomposition of cyclohexylhydroperoxide is carried out with the aid of a method described in EP-A-004105 or EP-A-092867.

The present invention will be further elucidated with reference to the following non-limiting examples.

Example I

A double-walled glass reactor (reactor volume equal to the liquid contents of 270 grams of cyclododecane (of 170° C.)) was used. The reactor was equipped with 4 baffles, a turbine mixer, coolers, a thermometer and two feed pipes. Melted cyclododecane was fed through one feed pipe, with the aid of a pump, at a rate of 732 g/h. A solution of the additive (2,6 -ditertiory-butylphenol) in melted cyclododecane was fed through the other feed pipe, with the aid of a second pump, at a rate of 90 g/h. The residence time in the reactor was 20 minutes. The feed rate of the additive was controlled so that the concentration of the additive in the reactor was 0.96 mmol/kg. The product was drained from the reactor via an overflow pipe with the aid of a control valve. The reaction temperature was 170° C. The speed of the stirrer was 2000 min$^{-1}$. Air was supplied at the bottom of the reactor via a gas distribution system at a rate of 30 Nl/h. Analyses of the effluent of the reactor showed that the selectivity towards cyclododecylhydroperoxide, cyclododecanol and cyclododecanone was 73.4, 4.4 and 15.2 mol %, respectively, (total 93 mol %) at a degree of conversion of cyclododecane of 4.4 mol %.

Comparative experiments A+B

Example I was repeated but no additive was added. Analyses of the effluent of the reactor showed that the selectivity towards cyclodecylhydroperoxide, cyclododecanol and cyclododecanone was 54.6, 13.3 and 18.8 mol %, respectively, at a degree of conversion of cyclododecane of 4.67 mol %.

This experiment was repeated. Analyses of the effluent of the reactor showed that the selectivity towards cyclododecylhydroperoxide, cyclododecanol and cyclododecanone was 51.7, 15.3 and 19.5 mol %, respectively, (total 86.5 mol %) at a degree of conversion of cyclododecane of 4.7 mol %.

Example II

Example I was repeated only now phenol was used as the additive. The feed rate of the additive was controlled so that the concentration in the reactor was 1.0 mmol/kg. Analyses of the effluent of the reactor showed that the selectivity towards cyclododecylhydroperoxide, cyclododecanol and cyclododecanone was 59.6, 14.8 and 18.7 mol %, respectively, (total 93.1 mol %) at a degree of conversion of cyclododecane of 4.4 mol %.

Example III

Example II was repeated only now the feed rate of the additive was controlled so that the concentration in the reactor was 0.8 mmol/kg and the cyclododecane feed was lowered in such an amount that the degree of conversion of cyclododecane was 4.7 mol %. Analyses of the effluent of the reactor showed that the selectivity towards cyclododecylhydroperoxide, cyclododecanol and cyclododecanone was 58.0, 12.5 and 17.8 mol %, respectively, (total 92.0 mol %).

Example IV

Example III was repeated only now the feed rate of the additive was controlled so that the concentration in the reactor was 0.48 mmol/kg. and the cyclododecane conversion was 5.1 mol %. Analysis of the effluent of the reactor showed that the selectivity towards cyclododecyl-hydroperoxide, cyclododecanol and cyclododecanone was 61.4, 6.3 and 15.3 mol %, respectively, (total 91.1 mol %).

Comparative Experiment C

Example V was repeated but no additive was added. The degree of conversion of cyclododecane was 5.1 mol % as in Example V. Analysis of the effluent of the reactor showed that the selectivity towards cyclododecylhydroperoxide, cyclododecanone and cyclododecanol was 48.6, 11.7 and 17.4 mol %, respectively (total 77.6 mol %).

Example V

Example I was repeated only now 2,6-ditertiary-butyl-4-methylphenol was used as the additive. The feed rate of the additive was controlled so that the concentration in the reactor was 0.94 mmol/kg. Analysis of the effluent of the reactor showed that the selectivity towards cyclododecylhydroperoxide, cyclododecanol and cyclododecanone was 59.2, 13.2 and 18.5 mol %, respectively, (total 91.9 mol %) at a degree of conversion of cyclododecane of 4.5 mol %.

Example VI

Example V was repeated. The feed rate of the additive was controlled so that the concentration in the reactor was 1.9 mmol/kg. Analysis of the effluent of the reactor showed that the selectivity towards cyclododecyl-hydroperoxide, cyclododecanol and cyclododecanone was 63.1, 8.6 and 17.0 mol %, respectively, (total 88.7 mol %) at a degree of conversion of cyclododecane of 4.6 mol %.

Example VII

Example I was repeated only now m-cresol was used as the additive. The feed rate of the additive was controlled so that the concentration in the reactor was 1.1 mmol/kg. Analyses of the effluent of the reactor showed that the selectivity towards cyclododecylhydroperoxide, cyclododecanol and cyclododecanone was 65.0, 8.1 and 18.5, respectively, (total 91.6 mol %) at a degree of conversion of cyclododecane of 4.3 mol %.

Example VIII

Example I was repeated only now 4-methoxyphenol was used as the additive. The feed rate of the additive was controlled so that the concentration in the reactor was 1.0 mmol/kg. Analysis of the effluent of the reactor showed that the selectivity towards cyclododecylhydroperoxide, cyclododecanol and cyclododecanone was 60.7, 13.2 and 17.8 (total 91.7 mol %) respectively at a degree of conversion of cyclododecane of 4.4 mol %.

Example IX

Example I was repeated only now 2, 4, 6-tritertiary-butylphenol was used as the additive. The feed rate of the additive was controlled so that the concentration in the reactor was 1.0 mmol/kg. Analyses of the effluent of the reactor showed that the selectivity towards cyclododeclylhydroperoxide, cyclododecanol and cyclododecanone was 65.7, 9.9 and 16.4 mol %, respectively, (total 92.0 mol %) at a degree of conversion of cyclododecane of 4.5 mol %.

Example X

Example I was repeated only now 2,4-ditertiary-butylphenol was used as the additive. The feed rate of the additive was controlled so that the concentration in the reactor was 1.1 mmol/kg. Analysis of the effluent of the rector showed that the selectivity towards cyclododecylhydroperoxide, cyclododecanol and cyclododecanone wa 67.4, 5.4 and 18.3 mol %, respectively, (total 91.1 mol %) at a degree of conversion of cyclododecane of 4.5 mol %.

Example XI

An experiment with cyclohexane was carried out in a setup equipped for tests under pressure similar to the setup described in Example I. 2,6-dibutyl-tertiary-4-methylphenol was used as the additive. The feed rate of the additive was chosen so that the concentration in the reactor was 1.25 mmol/kg. Analyses of the effluent of the reactor showed that the selectivity towards cyclohexylhydroperoxide, cyclohexanol and cyclohexanone was 92.3 mol % at a degree of conversion of cyclohexane of 3.5 mol %.

Example XII

Example XI was repeated only now phenol was used as the additive. The feed rate of the additive was chosen so that the concentration in the reactor was 0.6 mmol/kg. Analyses of the effluent of the reactor showed that the selectivity towards cyclohexylhydroperoxide, cyclohexanol and cyclohexanone was 91.5 mol % at a degree of conversion of cyclohexane of 3.4 mol %.

Example XIII

Example XII was repeated. The phenol concentration was 0.3 mmol/kg and the total selectivity was 91.9 mol % at a degree of conversion of cyclohexane of 3.5 mol %.

Comparative Experiment D

Example X was repeated only now without the addition of an additive. Analyses of the effluent of the reactor showed that the selectivity towards cyclohexylhydroperoxide, cyclohexanol and cyclohexanone was 89.4 mol % at a degree of conversion of cyclohexane of 3.4 mol %.

Example XIV

Example I was repeated. The feed rate of the additive was controlled so that the concentration in the reactor was 0.094 mmol/kg. Analyses of the effluent of the reactor showed that the selectivity towards cyclododecylhydroperoxide, cyclododecanol and cyclododecanone was 61.6, 12.1 and 18.4 mol %, respectively, (total 92.1 mol %) at a degree of conversion of cyclododecane of 4.4 mol %.

Example XV

Example I was repeated. The feed rate of the additive was controlled so that the concentration in the reactor was 0.48 mmol/kg. Analyses of the effluent of the reactor showed that the selectivity towards cyclododecylhydroperoxide, cyclododecanol and cyclododecanone was 68.0, 4.3 and 18.1 mol %, respectively, (total 90.4 mol %) at a degree of conversion of cyclododecane of 5.0 mol %.

Example XVI

Example I was repeated using 2,6-di-ter-butylphenol as the additive. At t=0 hr. no additive was added. After 3 hours of operation a sample was pulled from the reactor. The sample at 3 hours represents the results of an experiment without additive. After that initial three hour period (cumulative elapsed time of 3 hours), the additive concentration was controlled over the next four hours so that the concentration of the additive in the reactor was 0.09 mmol/kg. At the end of that period (cumlative elapsed time of 7 hours), the feed rate of the additive was controllably adjusted to obtain the concentration of the additive reported in Table I. The procedure was repeated every four hours. The additive concentration was increased from about 0.1 mmol/kg up to 10 mmol/kg as reported in Table I. Samples were taken at the end of each four-hour period. The selectivity in the first period to cyclododecanone, cyclododecanol and cyclododecylhydroperoxide was 87.8% at a conversion of 5.2 mol % of cyclododecane. The results of Example XVI are depicted in the FIG. 1. As can be seen, the selectivity increases up to 1 mmol/kg of additive after which the selectivity decreases. With respect to these results, addition of more than about 1 mmol of additive per kg of reaction mixture has no additional benefit.

TABLE I

| Period | Additive concentration (mmol/kg) | Increase in selectivity (% compared to period 1) |
|---|---|---|
| 1 | 0 | — |
| 2 | 0.09 | 2.7 |

TABLE I-continued

| Period | Additive concentration (mmol/kg) | Increase in selectivity (% compared to period 1) |
| --- | --- | --- |
| 3 | 0.48 | 3.2 |
| 4 | 0.96 | 3.3 |
| 5 | 3.00 | 2.7 |
| 6 | 5.0 | 1.9 |
| 7 | 9.9 | −1.6 |

What is claimed is:

1. A method for the continuous preparation of a mixture of a cycloalkanone, a cycloalkanol and a cycloalkylhydroperoxide comprising oxidizing their corresponding $C_6$ to $C_8$ cycloalkane in a continuous process, with the aid of an oxygen-containing gas, in the absence of a metal catalyst, at a temperature of 130° C. to 200° C., wherein said oxidation is at least partly carried out in the presence of between 0.002 and 2 mmol of a phenolic compound per kg of reaction mixture (mmol/kg), wherein said phenolic compound is represented by the formula (II):

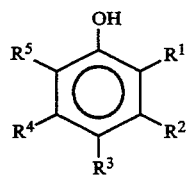

wherein $R^1$ through $R^5$ are, independently of one another, an —O—$R^6$ group or an $R^7$ group, wherein $R^6$ and $R^7$ are, independently of one another, H, a $C_1$ to $C_{30}$ organic group, or a $C_1$-$C_{30}$ organic group substituted with at least one group selected from the group consisting of ether, carbonyl, hydroxyl, amine, amide and ester; or wherein $R^1$ and $R^2$, or $R^2$ and $R^3$, or $R^3$ and $R^4$, or $R^4$ and $R^5$, together constitute an aliphatic or aromatic ring having 5, 6, 7, 8, 10 or 12 carbon atoms.

2. A method according to claim 1, wherein said phenolic compound contains one or more groups according to Formula (I)

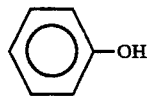

and is soluble in the cycloalkane.

3. A method according to claim 2, wherein said phenolic compound has a molecular weight of less than 1000 and has 1-5 aromatic rings.

4. A method according to claim 1, wherein the concentration of phenolic compound in the reaction mixture lies between 0.01 and 1 mmol/kg.

5. A method according to claim 1, wherein the concentration of phenolic compound ranges from 0.05 mmol/kg to 0.9 mmol/kg.

6. A method according to claim 1, wherein the concentration of the phenolic compound is less than 0.01 wt. % relative to the reaction mixture.

7. A method according to claim 1, wherein the temperature during the oxidation is between 160° C. and 190° C.

8. A method according to claim 1, wherein the pressure during the oxidation is between 0.1 and 5 MPa.

9. A method for the continuous preparation of a reaction mixture of a cyclohexanone, a cyclohexanol and a cyclohexylhydroperoxide, comprising oxidizing cyclohexane in a continuous process, with the aid of an oxygen-containing gas, in the absence of a metal catalyst, at a temperature of between about 130° C. and about 200° C., wherein said oxidation is at least partly carried out in the presence of between 0.002 and 2 mmol of phenol per kg of reaction mixture (mmol/kg).

10. A method according to claim 9, wherein the concentration of phenol ranges from 0.05 mmol/kg to less than 1 mmol/kg.

11. A method for the continuous preparation of a mixture of a cycloalkanone, a cycloalkanol and a cycloalkylhydroperoxide comprising oxidizing their corresponding $C_5$ to $C_{20}$ cycloalkane in a continuous process, with the aid of an oxygen-containing gas, in the absence of a metal catalyst, at a temperature of 130° C. to 200° C., wherein said oxidation is at least partly carried out in the presence of less than 0.01 wt. % of a phenolic compound relative to the reaction mixture, wherein said phenolic compound is represented by the formula (II):

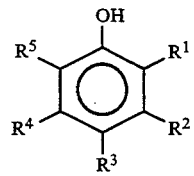

wherein $R^1$ through $R^5$ are, independently of one another, an —O—$R^6$ group or an $R^7$ group, wherein $R^6$ and $R^7$ are, independently of one another, H, a $C_1$ to $C_{30}$ organic group, or a $C_1$-$C_{30}$ organic group substituted with at least one group selected from the group consisting of ether, carbonyl, hydroxyl, amine, amide and ester; or wherein $R^1$ and $R^2$, or $R^2$ and $R^3$, or $R^3$ and $R^4$, or $R^4$ and $R^5$, together constitute an aliphatic or aromatic ring having 5, 6, 7, 8, 10 or 12 carbon atoms.

12. A method according to claim 11, wherein said cycloalkane has between 6 and 12 carbon atoms.

13. A method according to claim 11, wherein said phenolic compound contains one or more groups according to Formula (I)

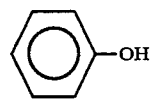

and is soluble in the cycloalkane.

14. A method according to claim 13, wherein said phenolic compound has a molecular weight of less than 1000 and has 1-5 aromatic rings.

15. A method according to claim 11, wherein the temperature during the oxidation is between 160° C. and 190° C.

16. A method according to claim 11, wherein the pressure during the oxidation is between 0.1 and 5 MPa.

* * * * *